United States Patent [19]

Kramer et al.

[11] 4,198,281

[45] Apr. 15, 1980

[54] SOLVATOR PLUG

[75] Inventors: David N. Kramer, Stevenson; Stephen E. Long, Baltimore; Alan A. Schneider, Reisterstown, all of Md.

[73] Assignee: Catalyst Research Corporation, Baltimore, Md.

[21] Appl. No.: 47,682

[22] Filed: Jun. 12, 1979

[51] Int. Cl.² ............................................. G01N 27/26
[52] U.S. Cl. .................................................. 204/195 R
[58] Field of Search .......... 204/195 R, 195 F, 195 M, 204/195 P

[56] References Cited

U.S. PATENT DOCUMENTS

| 4,017,373 | 4/1977 | Shaw ................................ 204/195 R |
| 4,025,412 | 5/1977 | La Conti .......................... 204/195 R |
| 4,132,616 | 1/1979 | Tantram ........................... 204/195 R |

Primary Examiner—T. M. Tufariello
Attorney, Agent, or Firm—Reed, Smith, Shaw & McClay

[57] ABSTRACT

The present invention relates to a solvator plug for replenishing aqueous or non-aqueous solvents in devices such as electrochemical sensor cells. The plug includes a housing adapted to communicatingly mount to a cell or the like which houses a selected solvent for absorption by the cell. The solvent is maintained within the housing by means of an absorbant material or membrane and is delivered by virtue of osmotic pressure differences.

5 Claims, 2 Drawing Figures

SOLVATOR PLUG

FIELD OF THE INVENTION

The present invention relates to a solvator plug for use in replenishing the solvent of electrochemical sensor cells.

BACKGROUND OF THE INVENTION

Electrochemical sensors are used in detecting and measuring the presence and amount of selected gas present in ambient atmosphere or work environment. Generally, these sensors are well known and utilize various electrode, electrolyte and solvent combinations which are known to be selectively sensitive to a desired gas or gases. These gases are usually introduced to the sensor by diffusion through a gas porous membrane, for example, a membrane made of sintered tetrafluoroethylene. The gas is either reduced or oxidized by the cell creating an electrochemical signal proportional to gas component in the sample area.

During the operation of the electrochemical sensors, the solvent, for example sulfuric acid or a non-aqueous organic solvent such as propylene carbonate, is lost through evaporation or permeation. This loss results in a decrease in the life of the sensor. One method of reducing the loss of solvent is place a means for humidifying the stream of gases directed to the sensor membrane. While the humidifier reduces evaporative losses and in some cases replaces lost aqueous solvents, the addition of such equipment greatly increases the size of the equipment. This size increase can be accepted in stationary equipment, but is generally unacceptable in portable monitoring type sensing equipment. Also, it has been found that adding humidity to the flow stream is not acceptable in times of low temperatures where the water can freeze resulting in a possible humidifier failure.

Another solution is to store the sensor device during nonuse in a chamber filled with vapors of the solvent. This solution is more practicable for portable sensor devices than for permanent monitoring type devices which are mounted at fixed locations or very large in size.

It is an object of the present invention to provide a device for replenishing the solvent which is adaptable to both permanent sensing monitors and portable sensing monitors. It is a further object to provide a device for replenishing the solvent of an electrochemical sensor which is convenient to use.

SUMMARY OF THE INVENTION

The solvator plug of the present invention comprises a housing having a attachment member adapted to communicatingly mount to the passageway of the sensor which leads to the electrochemical cell. The housing includes a chamber in which the selected solvent is stored. The solvent may be stored by means of an absorbent material, e.g., cotton or sponge as in the case of an aqueous solvent, or, e.g., glass-wool in the case of an organic solvent. Alternatively, the chamber may be defined by a permeable membrane which is positioned across the opening in the attachment member.

The solvator plug is attached to the sensor cell opening when the sensor is not in use. The vapors of the solvent contained in the plug is absorbed by the sensor by the difference in osmotic pressure. The absorption process usually continues during the period the plug is attached or positioned adjacent to the sensor cell gas inlet.

The size of the plug is relatively small so that it can be positioned on either a portable monitor or a permanent monitor. When respect to portable monitors, the solvator plug of the present invention can remain attached to the monitor during periods of non-use without affecting the portability of the monitor. Other advantages of the present invention will become apparent from a perusal of the following detailed description of a presently preferred embodiment showing the best mode contemplated taken in connection with the accompanying drawings.

DESCRIPTION OF PREFERRED EMBODIMENT

Figure 1:
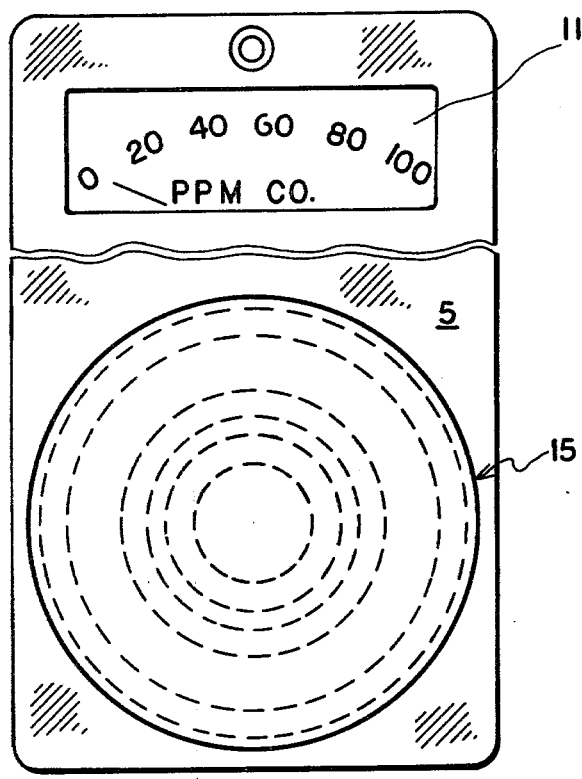
FIG. 1 is an elevation showing the solvator plug of the present invention attached to a portable electrochemical sensing device.
Figure 2:
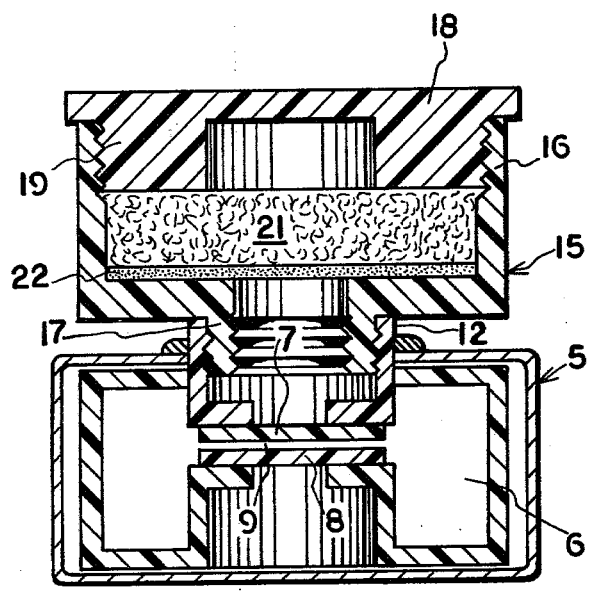
FIG. 2 is a sectional taken along line II—II of FIG. 1.

With reference to FIG. 1, a portable sensing device 5 is shown on which the solvator plug 15 of the present invention is attached. Sensing device 5 may monitor the presence and levels of carbon monoxide, for example. As shown in FIG. 2, sensing device 5 includes an electrochemical cell 6 having a first membrane 7 made from a sintered fluorocarbon and a second membrane 8 made from the same type of material. The first membrane includes a working electrode sintered thereto and the second membrane includes a reference and counter electrode. The electrolyte, $H_2SO_4$ in the case of carbon monoxide, is contained within annular cell 6 and in space 9 between membranes 7 and 8.

Cell 6 electrooxidizes the carbon monoxide to carbon dioxide in an amount proportional to the partial pressure in the sample area. The resulting electrochemical signal is amplified and temperature compensated to indicator meter 11 of monitor 5.

Other configurations of electrochemical sensing cells are found in use in which the relative positioning of the membrane and electrodes is different from that disclosed in FIG. 2. However, in all such electrochemical cells, a port is provided between the atmosphere to be measured and the electrochemical cell. It is to this inlet port that solvator plug 15 is mounted or juxtapositioned.

As shown in FIG. 2, solvator plug 15 comprises a housing 16 having attaching means 17 located at one end thereof. Attaching means 17, as shown, is threaded to threadably mount to inlet port 12 of electrochemical cell 6. The configuration of attaching means 17 is selected and designed for the size and type of inlet port to which the plug is to be mounted. Also, means 17 may be designed to removably fit housing 16 so that any number of different designs may be used. Normally, however, a plug 15 is used with only one particular monitor.

Housing 16 may include a removable cover 18 to refill the solvent. The solvent is preferably maintained in chamber 19 by means of an absorbent 21 such as glass-wool, cotton or a solvent permeable membrane 22 made from a sintered fluoro-carbon or like material. Alternatively, both means may be used as shown in FIG. 2. To maintain a leak tight seal where a permeable membrane is used, compression seals are included between cover 18 and membrane 22. These are not required when an absorbent material is used, alone or in combination with membrane 22.

It is clear that the solvator plug of the present invention may be otherwise designed within the scope of the appended claims; a preferred embodiment only having been shown and described in particularity.

What is claimed is:

1. A solvator plug for replenishing a solvent in the electrochemical sensing cell comprising:

(a) a housing having an attachment means adapted to be communicatingly mounted to the inlet port of a sensing cell;

b. a chamber for containing a solvent the vapor of which is adapted to be delivered to the sensing cell;

c. means for containing said solvent within the chamber but permitting the vapors thereof to diffuse from the chamber through said attachment means.

2. A solvator plug as set forth in claim 1 wherein said housing includes a removable cover to permit refilling said chamber with solvent.

3. A solvator plug as set forth in claim 1 wherein said means for containing said solvent consists of a permeable membrane sealingly positioned between the chamber and said attachment means.

4. A solvator plug as set forth in claim 1 wherein said means for containing said solvent comprises an absorbent positioned within said housing chamber.

5. A solvator plug as set forth in claim 4 wherein said means for containing said solvent includes a permeable membrane sealingly positioned between the housing chamber and said attachment means.

* * * * *